United States Patent
Schaefer

(10) Patent No.: US 9,308,377 B1
(45) Date of Patent: Apr. 12, 2016

(54) SYSTEM AND METHOD FOR TRANSMISSION OF ELECTRICAL SIGNALS IN IMPERFECTLY-CONDUCTING MEDIA

(75) Inventor: Philip R. Schaefer, Weaverville, NC (US)

(73) Assignee: Vortant Technologies, LLC, Weaverville, NC (US)

( * ) Notice: Subject to any disclaimer, the term of this patent is extended or adjusted under 35 U.S.C. 154(b) by 1035 days.

(21) Appl. No.: 11/250,828

(22) Filed: Oct. 13, 2005

Related U.S. Application Data

(63) Continuation-in-part of application No. 10/014,414, filed on Dec. 14, 2001, now Pat. No. 6,972,690.

(60) Provisional application No. 60/255,852, filed on Dec. 15, 2000.

(51) Int. Cl.
*A61N 1/372* (2006.01)
*H02J 7/02* (2006.01)
*A61N 1/375* (2006.01)

(52) U.S. Cl.
CPC ........ *A61N 1/37205* (2013.01); *A61N 1/37223* (2013.01); *A61N 1/37252* (2013.01); *H02J 7/025* (2013.01); *A61N 1/3756* (2013.01)

(58) Field of Classification Search
CPC ........... A61N 1/37252; A61N 1/37211; A61N 1/37235; A61N 1/37223; A61N 1/37205; A61N 1/3756; A61B 5/0031; H02J 7/025
USPC .................... 607/30, 32, 33, 60, 61
See application file for complete search history.

(56) References Cited

U.S. PATENT DOCUMENTS

| | | | |
|---|---|---|---|
| 3,841,312 A | 10/1974 | Corasanti | |
| 4,207,568 A | 6/1980 | MacLeod | |
| 5,467,011 A | 11/1995 | Hunt | |
| 6,236,886 B1 | 5/2001 | Cherepenin et al. | |
| 6,285,742 B1 | 9/2001 | Haumann et al. | |
| 6,754,472 B1 | 6/2004 | Willaims et al. | |
| 2004/0059386 A1* | 3/2004 | Yu | 607/2 |
| 2006/0085039 A1* | 4/2006 | Hastings et al. | 607/9 |

OTHER PUBLICATIONS

Jordan and Balmain, "Electromagnetic Waves and Radiating Systems", Prentice Hall, Inc., pp. 127-130 1968.
Urick, R.J., "Principles of Underwater Sound", McGraw Hill Book Company, New York, 1967 pp. 102-104.
Kilgore, Kevin, et al, "An Implanted Upper-Extremity Neuroprosthesis", Journal of Bone and Joint Surgery, vol 79-A. Nr.4. pp. 533-541, Apr. 1997.

(Continued)

*Primary Examiner* — Tammie K Heller
(74) *Attorney, Agent, or Firm* — Toering Patents PLLC

(57) ABSTRACT

A system for transmitting a signal through an imperfectly-conducting medium includes a transmitter station and a receiver station. The transmitter station has a transmitter and at least one conductor (electrode). The receiving station has at least one conductor (electrode) and a receiver. The transmitter causes a current to flow from the transmitter conductor to the receiver conductor through the imperfectly-conducting medium. Associated with the current flow is an electric field. Because the current flow varies with the signal, the electric field varies with the signal. The receiving conductor senses the electric field and provides a signal to the receiver which detects the signal to be transmitted. The receiving station then passes the signal to an output device to be output.

23 Claims, 27 Drawing Sheets

(56) References Cited

OTHER PUBLICATIONS

Loeb, Gerald E. et al, "BION system for distributed Neural prosthetic interfaces", Medical Engineering & Physics, pp. 10-18, Sep. 18, 2001.

Reilly, J. Patrick, "Electrical Stimulation and Electropathology" Cambridge University Press, pp. 126-128 1992.

Lampinen, Juoko et al, "Application of Bayesian Neural Network in Electrical Impedance Tomography", In Proc. IJCNN'99, Washington, D.C., USA, Jul. 1999.

* cited by examiner

SYSTEM AND METHOD FOR TRANSMISSION OF ELECTRICAL SIGNALS IN IMPERFECTLY-CONDUCTING MEDIA

This application is a continuation-in-part of U.S. patent application Ser. No. 10/014,414, filed Dec. 14, 2001, now U.S. Pat. No. 6,972,690 which claimed the benefit of U.S. Provisional Application No. 60/255,852 filed Dec. 15, 2000, which is hereby incorporated by reference herein in its entirety.

FIELD OF THE INVENTION

The present invention relates to transmitting signals in imperfectly-conducting media. More specifically, the present invention relates to using an electric field to transmit signals through or near water, the earth, or other imperfectly-conducting media.

BACKGROUND OF THE INVENTION

Transmitting signals through imperfectly-conducting media is a notoriously difficult problem. A major reason for this difficulty is that imperfect conductors severely attenuate radio waves traveling through them. This is because, as discussed in Jordan and Balman, "Electromagnetic Waves and Radiating Systems", Prentice-Hall, 1968, Chapter 5, imperfect conductivity (partial conductivity) causes attenuation of the electric field component of the oscillating electric/magnetic energy wave, such as a propagating radio signal. This attenuation renders radio communication under water nearly impossible. Even where possible, such communication is generally impractical. Consequently, its use is limited to only a few applications. For example, using very low frequencies and very high power levels, radio waves can be transmitted into deep water whereby communications with submarines generally require high power transmitters that transmit signals containing frequencies below approximately 10 KHz.

Largely because of the difficulties associated with transmitting electromagnetic waves through imperfectly conducting media, most systems that try to transmit signals through such media use acoustic energy, rather than electromagnetic energy. Examples of such systems are found in the "DiveLink" ultrasonic system sold by Divelink, Inc. and the "Buddy Phone" sold by Ocean Technology, Inc. However, acoustic systems also suffer from a number of drawbacks. One drawback is that, like electromagnetic waves, acoustic waves suffer significant attenuation in water or earth. See Urick, R., J., "Principles of Underwater Sound", 3d Edition, McGraw-Hill Book Company, New York, 1983.

Another drawback is that natural or man-made noise can interfere with acoustic systems. For example, acoustic noise from surf or storms or engine noise from nearby boats can dramatically affect the performance of underwater acoustic communication Another problem with acoustic signaling arises from reflections that can occur when properties of the medium through which an acoustic wave propagates vary. An exemplary change in a property of a medium is a thermocline in water. Although useful in some applications such as SONAR, reflection of acoustic waves in a communication system is generally detrimental to the communications. For example, due to the relatively slow speed of sound propagation in water, reflection of acoustic waves can lead to severe multipath interference, which causes degradation in intelligibility and loss of communication bandwidth. Moreover, in some cases, the reflection is so severe that it causes complete loss of signal results due to reflection of the acoustic signal wave away from the desired transmission path.

There has been little research exploring the use of the imperfect conductivity of the medium as a beneficial feature, rather than a detriment, to communication systems. In U.S. Pat. No. 4,207,568 to MacLeod, a communication link is described that uses the bulk conductivity of water for one side of a transmission circuit, and a water-filled, flexible insulating tube as the other side of the circuit. Although this approach avoids the problems of non-flexible conductive wires, it requires the tube to make a physical connection between the ends of the communication link. Consequently, it is limited in its application.

There also has been work done in transmitting data using the body to form a personal-area network. This is essentially using the body as an antenna. For example, in U.S. Pat. No. 6,754,472 B1 to Williams et al, a network for a variety of small devices worn by a person is described. However, these networks do not provide for stimulation output or for other outputs to affect the body. Also, the frequencies described in the Williams et al patent are within a range that would cause shock and unwanted muscular stimulation at the levels required of the present invention.

The BION system (See Loeb, et. al., Journal of Medical Engineering and Physics, Vol. 23, pages 9-18) is a wireless system to provide stimulation outputs from a small, implanted system. However, the BION system does not use an electrical transmission method, instead the BION system uses a magnetic field that is picked up by a receiving coil in the implanted device. This requires a large coil with very high current to be placed on the body in close proximity to the receiving device. Providing this coil can be very cumbersome.

SUMMARY OF THE INVENTION

The present invention solves the foregoing problems of conventional communication systems by creating an electric field, and using the electric field to transmit signals through an imperfectly-conducting medium. The present invention changes the properties of the electric field in accordance with the desired signals to be transmitted.

In one embodiment of the present invention, signals are transmitted within and through an imperfectly conducting media by use of an electric field. The present invention includes one or more conductors that are used at the transmitter to create an electric field in the medium. Similarly, one or more conductors are used at the receiver to extract the signal from the medium. Rather than using electromagnetic radiation, which relies on the interchange of energy between traveling magnetic and electric fields, and hence, is severely attenuated by any conductivity in the medium, the present invention uses the electric field alone as its basis of operation. Rather than attenuating the field, the conductivity of the medium is compatible with the flow of conductive current, which accompanies the desired electric field.

In another embodiment of the present invention, signals are generated at or near the surface or boundary of the imperfectly conducting medium. Using such a configuration, the present invention can also be used in this embodiment as a relatively efficient antenna for propagating radio signals along the surface or boundary of the medium, such as along the surface of a body of water. When used in this way, the present invention creates an electric field using one or more conductors, but the generation and propagation of electromagnetic energy is possible in the nearby non-conducting medium, such as the atmosphere adjacent to the conducting medium.

In another embodiment of the present invention, the human body is used as the imperfectly-conducting medium to form a wireless electrical stimulation system. In this embodiment of the present invention, wireless signals are transmitted from a transmitter and received at small receivers embedded in the body. The receivers use the energy of the transmitted signal and/or the commands encoded by the signal to cause electrical stimulation of the body, for purposes such as neuroprosthetics, cardiac pacemakers, etc. In this discussion, the term "electrode" will be used interchangeably with the term "conductor", because this terminology is more common in the medical field.

As described below, the operations discussed above in this summary may be performed using essentially identical apparatus.

DETAILED DESCRIPTION OF THE INVENTION

The present invention is based on the creation of an electric field within an imperfectly-conducting medium (a partially conductive medium). The electric field can also be created adjacent to a boundary of the imperfectly-conducting medium.

Figure 1:
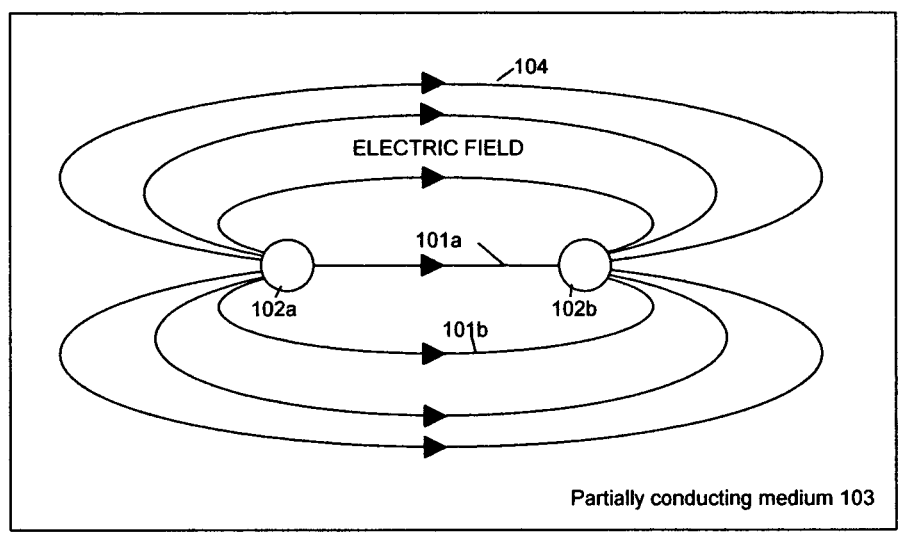
FIG. 1 is a schematic diagram illustrating the electric field accompanying a current flow.

FIG. 1 is a schematic diagram illustrating the basis of operation of the present invention. As illustrated in FIG. 1, two conductors 102a and 102b are submerged in an imperfectly-conducting medium 103. An electrical signal is applied between conductors 102a and 102b. A current flows between conductors 102a and 102b as a result of the applied electric signal. FIG. 1 shows the lines of conduction current 101a, 101b that result between conductors 102a and 102b. The lines of current flow 101a and 101b actually extend to infinity within the medium. The lines shown in FIG. 1 depict only a few typical lines of current flow.

As is well known, electrical current flow is associated with an electric field along which the current flows. The lines of conduction also indicate the geometry of an electric field 104 that exists in imperfectly-conducting medium 103. Electric field 104 exists along the lines of current flow in the partially-conducting medium to cause that current flow.

Preferably, an AC signal is applied to conductors 102a and 102b to generate an alternating electric field. The electric field produced by the conductors corresponds to the lines of conduction shown in FIG. 1. Although radio frequency radiation over significant distances is not feasible through the imperfectly-conducting medium, the electric field alone can be used for signal transmission. Thus, the present invention uses the electric field associated with the electrical current flow to transmit the signal, rather than relying upon electromagnetic wave propagation.

The function of conductors 102a and 102b is analogous to the function of an antenna in a conventional radio station. However, the mechanism by which the conductors function is substantially different than a radio antenna. Conductors 102a and 102b are designed to have relatively large surface area, so that conduction between the conductors is as large as possible to maximize electric field generation and current flow. In standard antenna designs that may appear similar to the conductor pair 102a and 102b, but used in the air (for example, an end-loaded dipole antenna), essential radiation is expected from the wires or tubes leading to the conductors. In the case of a conventional antenna therefore, the conductors typically serve as capacitive, rather than conductive, elements.

In contrast to standard antenna designs, in the present invention, the leads to the conductors 102a and 102b do not directly generate the electric field, which is the basis of operation of the device. Instead, the important characteristic of the present invention is the generation of the electric field that is the basis of the operation of the device by the conduction of electrical current between the conductors, which would be an undesirable effect in an electromagnetic antenna.

Another characteristic of the transmitting and receiving conductors in the present invention is the low overall impedance of the transmitting and receiving conductor pairs. Because of the conductive nature of the transmission mechanism, the impedance of a pair of conductors, of small dimensions, (tens of centimeters) closely spaced (several meters) and at reasonably low frequencies (less than 100 kHz), in conductive media such as water, will have a primarily resistive impedance of a fraction of an ohm to tens of ohms. This impedance is radically different than a similar-looking antenna in air, due to the different function of the parts. Because the received signal is developed across a low impedance, there will be more signal power available between the conductors at the receiver than between similar conductors in air.

Figure 2:
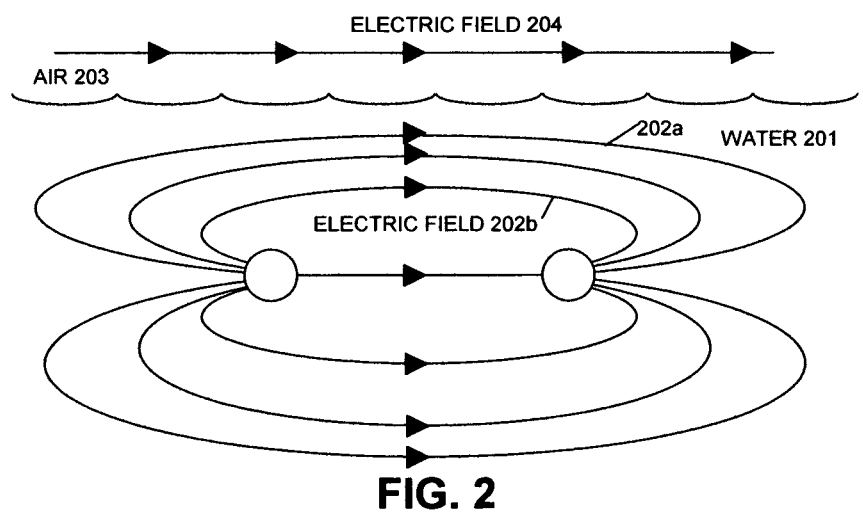
FIG. 2 is a schematic diagram illustrating the electric field accompanying a current flow that is constrained by medium boundaries.

FIG. 2 depicts the conduction and fields created with a device of the present invention when located near the surface of an imperfectly conducting medium 201, for example, water. FIG. 2 shows the lines of electric field and conductive current flow 202a, 202b in water 201 near the surface of the water. As shown in FIG. 2, near the surface, the field is warped somewhat to remain within the conductor because conduction current cannot flow through air. However, the electric field at the surface of the water induces an electric field 204 in the air 203 just above the water. In-air 204 field becomes the source of a radiated radio wave, if the frequency is high enough, for example, for frequencies above 100 kHz.

Figure 3:
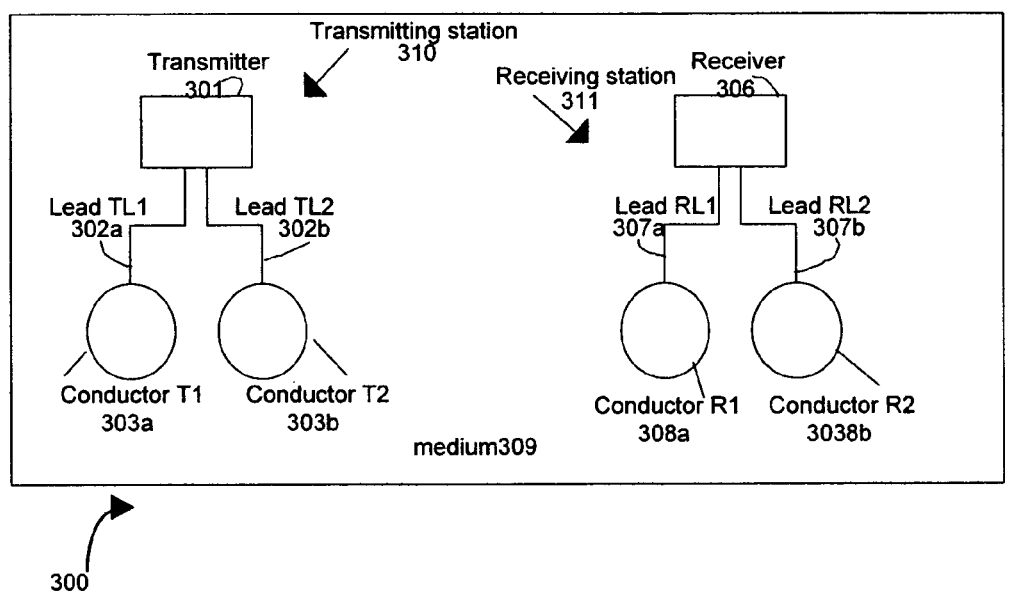
FIG. 3 is a schematic diagram for using an electric field to transmit and/or receive signals in an imperfect conductor according to the present invention.

To transmit signals using the present invention, at least one transmitter and at least one receiver station are required. FIG. 3 is a schematic diagram of a preferred embodiment of a signal transmission system 300 according to the present invention. As shown in FIG. 3, the system 300 is preferably contained within an imperfectly conducting medium 309. Exemplary imperfect conducting mediums include water and earth. The system 300 includes a transmitting station 310 and a receiving station 311. The transmitting station 310 includes a transmitter 301. The transmitter 301 generates electrical signals on leads 302a and 302b. The leads 302a and 302b are preferably insulated to minimize conduction of current from other than the intended transmitter conductors 303a and 303b. The leads 302a and 302b are preferably the inner and outer conductors of a length of coaxial cable such as RG-58A. Alternatively, the leads 302a and 302b can be lengths of insulated wire such as #22 stranded wire. The leads 302a and 302b are connected to the transmitter conductors 303a and 303b.

The receiving station 311 comprises a receiver 306. The receiver 306 receives input signals via leads 307a and 307b. The leads 307a and 307b are preferably of the same type as leads 302a and 302b. The leads 307a and 307b are connected to receiver conductors 308a and 308b.

The transmitter conductors 303a and 303b create an electric field in the imperfectly-conducting medium 309. The receiver conductors 308a and 308b detect an electric field in the imperfectly-conducting medium 309, due to the potential difference caused by the field at the locations of the receiver conductors 308a and 308b. Generally, as the surface area of the transmitter and receiver conductors increases, the strength of the generated and/or received signal also increases. The transmitter and receiver conductors can be made of highly-conductive materials such as metals. One such metal that can be used in the present invention is aluminum. Alternatively, less well-conducting substances can be used.

In an embodiment of the present invention, aluminum sheets are used for conductors 303a, 303b, 308a, and 308b. Preferably, the aluminum sheets have dimensions of approximately 50 cm by 30 cm. Other shapes and materials can be used, depending on the application. For short-range or high-power applications, the conductors could be smaller. The foregoing structure and function described for the transmitter conductors 303a and 303b and the receiver conductors 308a and 308b also apply to the conductors described below in each of the embodiments of the present invention.

The distance between the transmitter conductors 303a and 303b and between receiver conductors 308a and 308b also affects performance of a transmission system according to the present invention. For a portable system, the distance between the transmitter conductors 303a and 303b, and the distance between the receiver conductors 308a and 308b is preferably 3 meters.

Figure 4:
FIG. 4 is a schematic diagram of an orientation of the conductors according to an embodiment of the present invention.

The orientation of transmitting and receiving conductors can also affect the performance of signal transmission according to the present invention. Generally, signals are strong when the conductors are aligned in a collinear array. FIG. 4 is a schematic diagram illustrating a collinear orientation of the conductors to achieve a relatively high signal strength. In FIG. 4, transmitter conductors 401a and 401b are shown aligned collinear to receiver conductors 402a and 402b. For clarity, the leads and transmitter and receiver electronics are not shown in this diagram, but are as described above.

Figure 5:
FIG. 5 is a schematic diagram of an orientation of the conductors according to another embodiment of the present invention

Strong signals are also present when the conductors are aligned in a broadside manner. FIG. 5 is a schematic diagram illustrating a broadside alignment of the conductors. In FIG. 5, transmitter conductors 504a and 504b are shown in broadside orientation with respect to receiver conductors 506a and 506b.

Figure 6:
FIG. 6 is a schematic diagram of an orientation of the conductors according to yet another embodiment of the present invention.

Signals are generally weakest when the conductors are aligned perpendicular to one another. FIG. 6 is a schematic diagram illustrating a perpendicular alignment of transmitter and receiver conductors. In FIG. 6, transmitter conductors 601a and 601b are shown oriented perpendicular to receiver conductors 602a and 602b.

Figure 7:
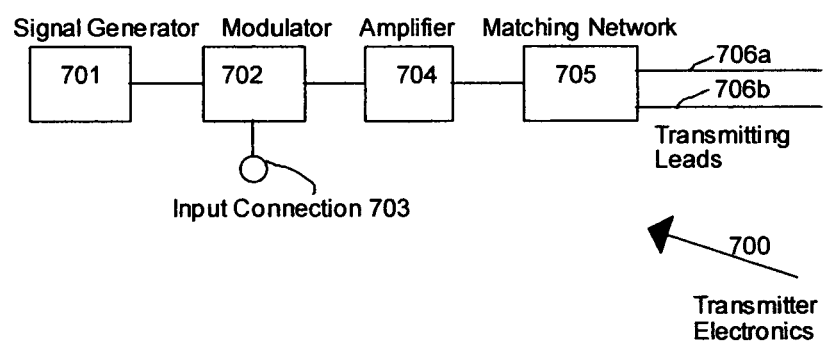
FIG. 7 is a schematic diagram of a transmitter according to an embodiment of the present invention.

FIG. 7 is a schematic diagram of a transmitter 700 according to an embodiment of the present invention. A desired communication signal or other input signal is applied to input connection 703. A signal generator 701 generates a carrier signal. Preferably, the carrier signal has a carrier frequency in the range from 10 Hz to 100 MHz. For most applications, the carrier frequency falls in the range from 5 kHz to 10 MHz. For transmission of signals within and through a medium such as water, the low end of the frequency range is preferred. For transmission of signals along the surface of the medium, the higher end of the frequency range is preferred. The carrier signal can be generated using a crystal-controlled oscillator. Generation of a carrier signal using a crystal-controlled oscillator is well-known to those skilled in the art.

A modulator 702 modifies the signal in accordance with a desired modulation mode. The preferred modulation mode is frequency shift keying (FSK). The modulated signal is applied to a power amplifier 704. Power amplifier 704 can be a circuit using well-known audio amplifier integrated circuits, for example, National Semiconductor, Inc.'s LM384. The power amplifier 704 increases the signal strength. For short-range, portable communication, the power amplifier 704 preferably increases signal strength to the 0.1-to-5-watt range. For longer-distance communication, the power amplifier 704 may need to increase signal strength to significantly higher levels.

A matching network 705 couples the amplified signal to transmitting leads 706a and 706b. The transmitting leads 706a and 706b are connected to the transmitter conductors. For fresh water transmission, the matching network 705 is preferably a 1:4 impedance ratio broadband transformer. For saltwater transmission, the matching network 705 is preferably a 4:1 impedance ratio broadband transformer. It will be apparent to one of ordinary skill in the art that other circuits, for example, those used in audio or RF designs, can be adapted for use in the transmitter 700 to provide electrical current to the leads 706a and 706b.

Figure 8:
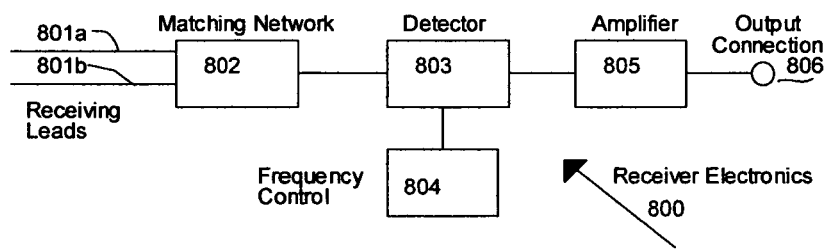
FIG. 8 is a schematic diagram of a receiver according to an embodiment of the present invention.

FIG. 8 is a schematic diagram of a receiver 800 according to an embodiment of the present invention. A pair of leads 801a and 801b is connected to the receiver conductors. The other end of the leads 801a and 801b are coupled to an impedance matching network 802. For use in fresh water, the impedance matching network 802 is preferably a 1:20 impedance ratio broadband transformer. For use in saltwater, the impedance matching network 802 is preferably a 1:300 impedance ratio broadband transformer.

The transformed signal is applied to a detector 803. When the preferred FSK modulation is used, the detector 803 is preferably an FSK detector to demodulate the received signal. When other modulation techniques are used, the detector 803 will use their corresponding demodulation techniques. The detector 803 detects a carrier frequency of the received signal. A frequency control 804 locks to the received carrier frequency to assist the detector 803 with detection. The frequency control 804 preferably is a crystal-controlled oscillator set to be compatible with the transmitter frequency (e.g., of transmitter 700). Techniques for detecting and demodulating signals received by the receiver 800 are well-known to those skilled in the art. The detected output is amplified by an amplifier 805 and provided through an output connection 806. The output connection 806 can be coupled to any desired output device including, for example, speakers, headphones, tape recorders, computer mass-storage devices or any other output device. It would be apparent to those skilled in the art that other circuits and/or techniques known to those skilled in the audio or RF designs can be adapted for use in the receiver 800 to detect the electrical inputs on leads 801a and 801b, and to provide output to the output connector 806.

Figure 9:
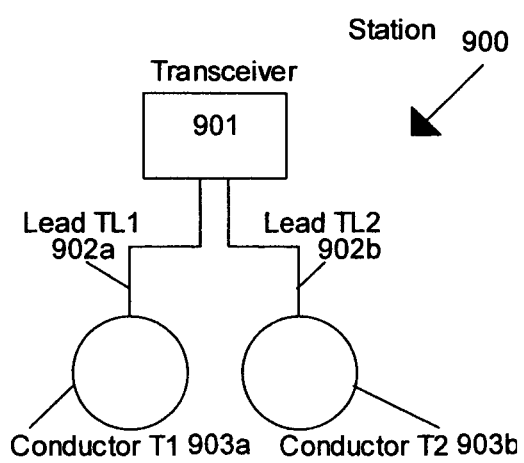
FIG. 9 is a schematic diagram of a transceiver for using an electric field to transmit and/or receive signals according to the present invention.

FIG. 9 is a schematic diagram of a transceiver station 900 according to an embodiment of the present invention. The transceiver station 900 performs both the transmitter and receiver functions in a single unit. Because bi-directional communication is desired, both transmitting and receiving functions are contained in a transceiver 901. The transceiver 901 is connected to conductors 903a and 903b by leads 902a and 902b, respectively.

Figure 10:
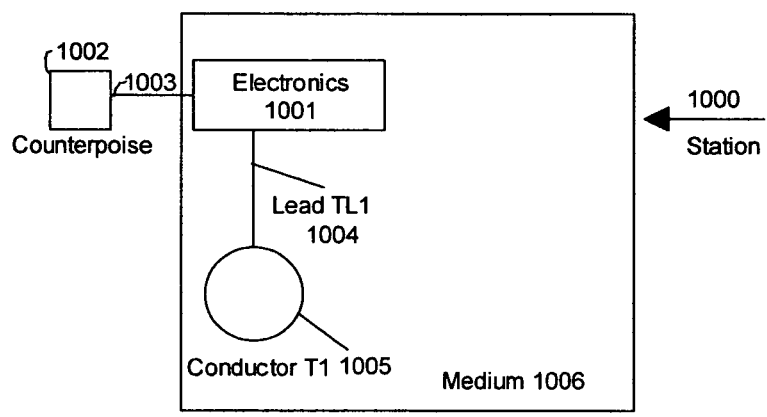
FIG. 10 is a schematic diagram of an embodiment of the present invention using one conductor and a counterpoise.

FIG. 10 is a schematic diagram of an embodiment of the present invention having a communication station 1000 that uses only a single conductor in the medium. The communication station 1000 includes electronics 1001 that perform the bulk of communication. The electronics 1001 can be a transmitter, a receiver or a transceiver. The electronics 1001 is connected via a lead 1004 to a single conductor 1005. The communication station 1000 also includes a counterpoise 1002.

The counterpoise 1002, also referred to as a "virtual ground," is preferably located external to the medium 1006, such as in the air. Alternatively, the counterpoise 1002 is contained in an enclosure with the electronics 1001. The counterpoise 1002 is coupled to the electronics 1001 via a lead 1003. The counterpoise 1002 provides an electrical balance for the conductor 1005. Thus, the counterpoise 1002 allows the single conductor 1005 to create and/or detect an alternating electric current and corresponding electric field in the medium 1006.

The counterpoise 1002 can be any device that accepts current from the electronics 1001. Preferably, the counterpoise 1002 is a conductive object such as a length of wire. Alternatively, the counterpoise 1002 can be a system ground of the electronics 1001, other conductive objects, or any other ground, preferably isolated from the medium 1006.

Figure 11:
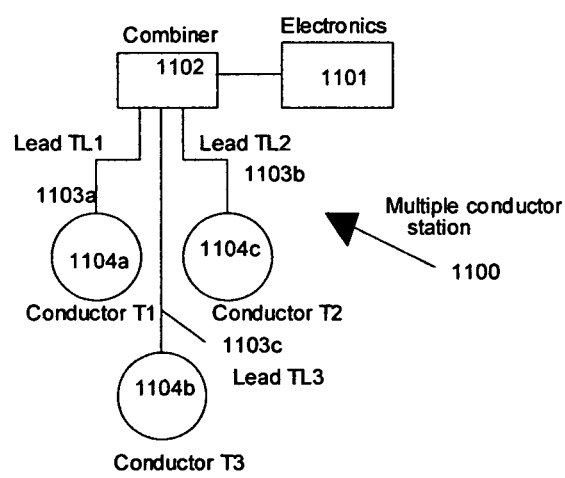
FIG. 11 is a schematic diagram of a multi-conductor unit for transmitting and/or receiving signals using an electric field according to an embodiment of the present invention.

FIG. 11 is a schematic diagram of a multi-conductor station 1100 according to an embodiment of the present invention. The multi-conductor station 1100 has more than two transmitter, receiver, or bi-directional conductors. The multi-conductor station 1100 includes electronics 1101. The electronics 1101 can be a receiver, transmitter, or transceiver. The electronics 1101 is connected to a combiner 1102. The combiner 1102 is connected to two or more conductors 1104a, 1104b, and 1104c through respective leads 1103a, 1103b, and 1103c.

The combiner 1102 is used to select and/or add the contributions of the conductors 1104a, 1104b, or 1104c. Preferably, the combiner 1102 is a switch that can connect any two of the conductors 1104a, 1104b, or 1104c to the electronics 1101. With the combiner 1102, the present invention can be used as a beam-steering mechanism to select various directional characteristics of the electronics 1101. Alternately, the combiner 1102 can be implemented as a resistive or reactive adder to obtain a wider range of directional characteristics. As described in FIGS. 4, 5, and 6, the present invention has its greatest response in a direction collinear with the selected or most highly contributing conductors 1104a, 1104b, and/or 1104c.

Figure 12:
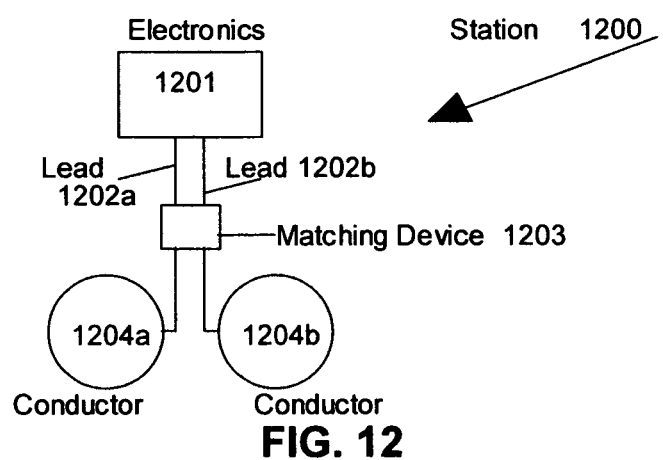
FIG. 12 is a schematic diagram of an embodiment of the present invention using impedance matching.

FIG. 12 is a schematic diagram of a station 1200 according to a preferred embodiment of the present invention that uses impedance matching to account for conductivity variations in a medium that exhibits, for example, a very high or very low conductivity. For example, saltwater is a medium that exhibits a relatively high conductivity. The station 1200 includes electronics 1201. The electronics 1201 can be a transmitter, a receiver, or a transceiver. The electronics 1201 is connected through a pair of leads 1202a and 1202b to a matching device 1203. The matching device 1203 has terminals that are coupled to conductors 1204a and 1204b, respectively. When the present invention is implemented to such media, the impedance of the transmitter and/or receiver conductors 1204a and 1204b can differ significantly from that of a standard lead material. Standard lead materials include, for example, coaxial cable. The matching device 1203 accounts for this difference. The matching device 1203 is placed near the conductors 1204a and 1204b. Using coaxial cable leads of approximately 50 ohms, for example, in saltwater the matching device 1203 is preferably a 1:25 impedance ratio broadband transformer. It will be apparent to one of ordinary skill in the art that other impedance-matching circuits known to those skilled in audio or RF designs can be adapted for use as the matching device 1203.

The station 1200 can be implemented as a single conductor or multi-conductor device as described above. In either case, one or more matching devices are used to couple the conductor or conductors to the leads.

Figure 13:
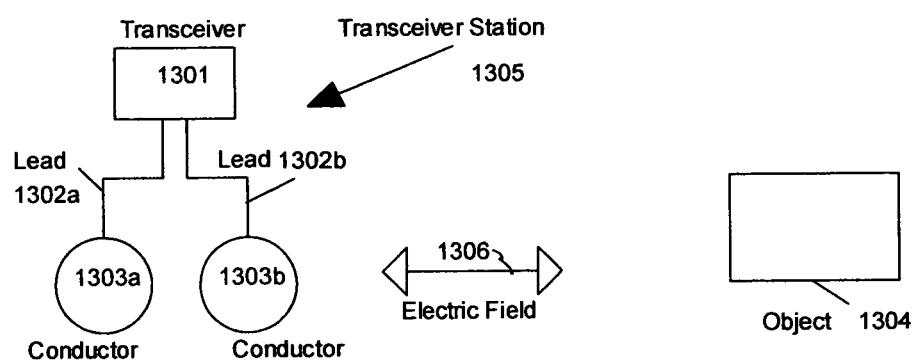
FIG. 13 is a schematic diagram of an embodiment of the present invention for detecting objects.

FIG. 13 is a schematic diagram of a transceiver station 1305 that is configured to detect objects according to an embodiment of the present invention. The transceiver station 1305 can be a single transceiver station 1305, as shown in FIG. 13. Alternatively, a separate transmitter, such as transmitter station 310, or a separate receiver station, such as receiver station 311, each of which is described above with reference to FIG. 3, could be used. The transceiver station 1305 includes a transceiver 1301. The transceiver 1301 is connected to conductors 1303a and 1303b through leads 1302a and 1302b, respectively. An electrical field 1306 is created by the conductors 1303a and 1303b. The presence of an object 1304 causes a change in the electric field 1306. This change, in turn, causes a change in the electric field 1306 sensed by the conductors 1303a and 1303b. The change is reflected in the signal detected in the receiver section of the transceiver 1301.

The transceiver 1301 preferably transmits and detects pulsed signals to enable it to detect objects. Alternatively, the transceiver 1301 can transmit and detect continuous waves (CW). One use of the present invention for detection of objects is to detect objects under water.

Using a multi-conductor station, such as the multi-conductor station 1100, the direction of a detected object 1304 can be determined by directional arrays. The distance to the object 1304 is preferably determined through triangulation by using the directions measured by multiple transceiver stations 1305. Triangulation techniques are well known to those skilled in the art. Alternatively, a time-delay technique can be used to measure the time at which the change in field is detected at the transceiver station 1305.

Figure 14:
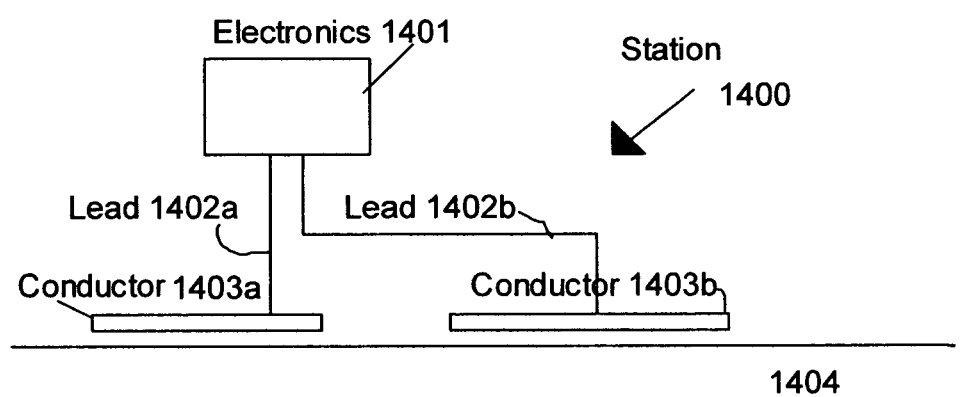
FIG. 14 is a schematic diagram of an embodiment of the present invention in which the conductors are placed at or near the boundary of an imperfectly-conducting medium.

FIG. 14 is a schematic diagram of a station 1400 for transmitting signals at or near a medium boundary according to an embodiment of the present invention. Station 1400 includes electronics 1401. The electronics 1401 can be a receiver, a transmitter, or a transceiver. The electronics 1401 is connected via leads 1402 to conductors 1403a and 1403b, respectively. The conductors 1403a and 1403b are not submerged or embedded within imperfectly-conducting medium 1404. Rather, one or more of the conductors 1403a and 1403b are located at or near the surface of the medium 1404. Where the medium 1404 is the earth, the conductors 1403a and 1403b are preferably aluminum plates having dimensions of approximately 50 cm by 30 cm. Further, the conductors 1403a and 1403b are placed at a height of from 0 to 5 cm above the surface of the medium 1404. With the station 1400, the present invention can be used for applications that require signaling to or from devices at or below the surface of the medium 1404. For example, where the medium 1404 is the earth, the present invention can be used to communicate with devices below the surface of the earth.

Figure 15:
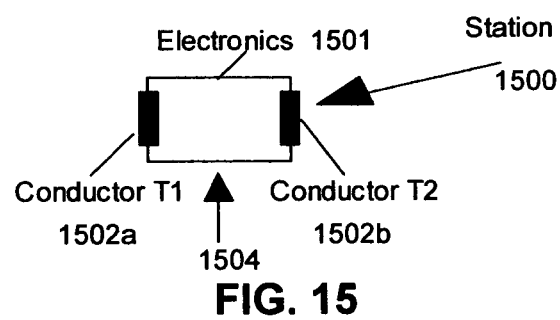
FIG. 15 is a schematic diagram of an embodiment of the present invention in which the conductors are self-contained.

FIG. 15 is a schematic diagram of a station 1500 having self-contained conductors according to an embodiment of the present invention. The station 1500 has electronics 1501. The electronics 1501 can be a transmitter, a receiver, or a transceiver. Rather than use leads to connect the electronics 1501 to the conductors 1502a and 1502b, the station 1500 contains the electronics 1501 and the self-contained conductors 1502a and 1502b. The conductors 1502a and 1502b are preferably aluminum panels that are attached to an insulated case. Preferably, the aluminum panels have a size of 15 cm by 10 cm, although other sizes can be used. Preferably, the insulated case is the case housing the electronics 1501. Preferably, the insulated case is made out of polyethylene.

Alternatively, the electronics 1501 could be housed in a case made out of a conductor such as aluminum. In this embodiment, the conductive case is used as the conductor. Preferably, the aluminum case has dimensions of 15 cm by 10 cm by 5 cm.

One or more external conductors and associated leads can perform the function of the conductor 1502b. Thus, the station 1500 can be implemented as a single conductor communication station.

Figure 16:
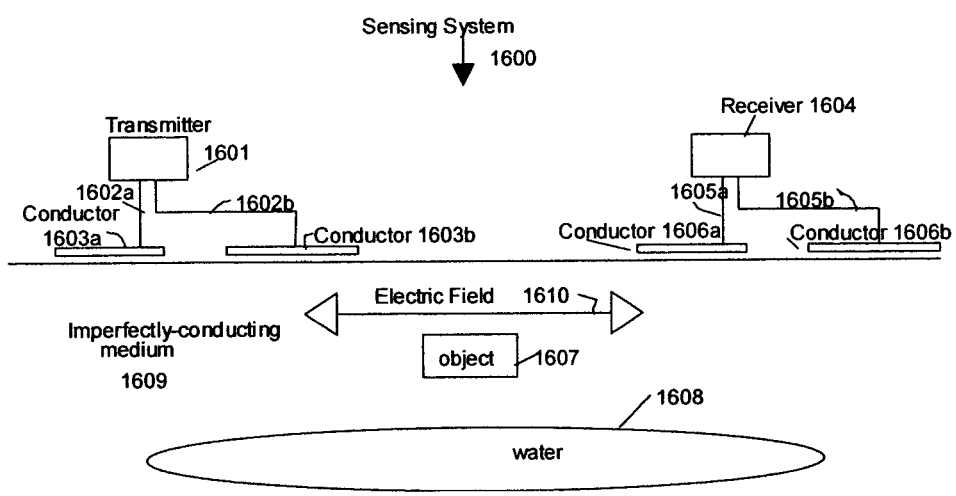
FIG. 16 is a schematic diagram of a sensing system according to an embodiment of the present invention.

FIG. 16 is a schematic diagram of a sensing system 1600 according to another embodiment of the present invention. The sensing system 1600 includes a transmitter 1601. The transmitter 1601 is coupled to conductors 1603a and 1603b through leads 1602a and 1602b, respectively. The conductors 1603a and 1603b generate an electric field 1610. The electric field 1610 induces currents in conductors 1606a and 1606b. The conductors 1606a and 1606b are coupled to a receiver 1604 through leads 1605a and 1605b, respectively. As described below, the sensing system 1600 senses changes in the electric field 1610 to determine properties of the medium being analyzed.

The sensing system 1600 can be used, for example, to measure properties of a medium 1609. These properties include bulk or average properties of the medium, such as conductivity. Heterogeneous properties of the medium such as the presence of an object 1607 in the medium or the presence of large structures such as underground water 1608 can be detected using the embodiment of the present invention shown in FIG. 16.

The electric field 1610 is not localized to a single line of sight. Therefore, the greater the distance between the transmitter conductors 1603a and 1603b and the receiver conductors 1606a and 1606b respectively, the deeper into the medium a major portion of the electric field 1610 will impinge, and thus the deeper into the medium data can be gathered.

Preferably, to obtain information about a structure beneath the surface, signal strength measurements are made at the receiver 1604 at various distances between the transmitting conductors 1603a and 1603b and the receiver conductors 1606a and 1606b. These signal strength measurements can be used to generate a plot of signal strength versus conductor spacing. The slope of the plot indicates the change in conductivity as a function of depth. The sensing system 1600 can be calibrated by comparing the slope versus spacing characteristics to slope versus spacing characteristics of known regions.

Figure 17:
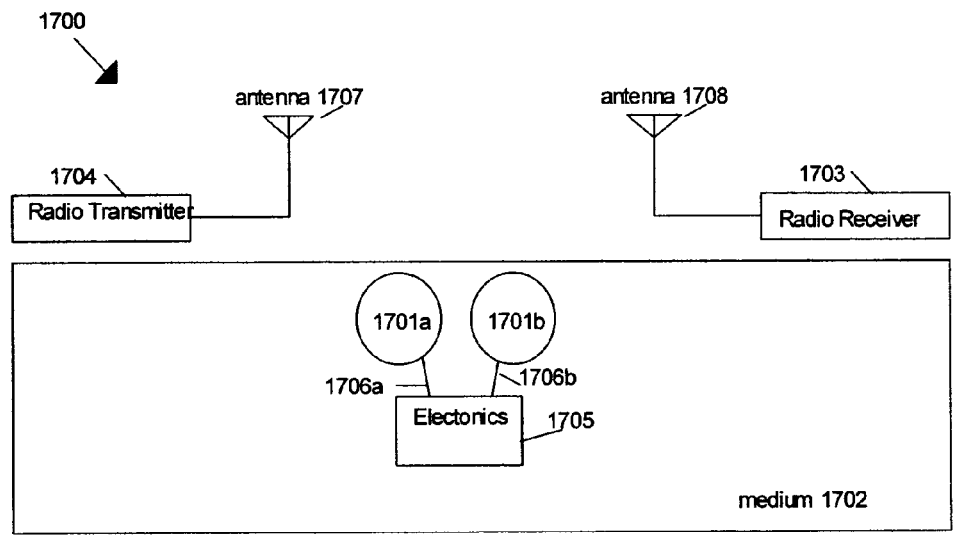
FIG. 17 is a schematic diagram of a system for using the present invention in conjunction with conventional radio transmitters or receivers.

FIG. 17 is a schematic diagram of a system 1700 that uses the present invention to communicate with a conventional radio transmitter or receiver. The system 1700 includes electronics 1705. The electronics 1705 can be a receiver, a transmitter, or a transceiver. A pair of leads 1706a and 1706b couples a pair of conductors 1701a and 1701b respectively. Preferably, the conductors 1701a and 1701b are located near the surface of the imperfectly-conductive medium 1702. When so located, the electric field produced by the conductors 1701a and 1701b at the surface will generate electromagnetic waves, which can propagate outside the imperfectly-conductive medium and be received at a conventional radio receiver 1703 with a conventional radio antenna 1708. Likewise, radio signals generated by a conventional radio transmitter 1704, using a conventional radio antenna 1707, can be received by the conductors 1701a and 1701b by the inverse mechanism. This configuration of the invention is most practical when the conductors 1701a and 1701b are located quite near the surface, preferably within one to two meters, and frequencies are relatively high, preferably above 100 kHz.

Figure 18:
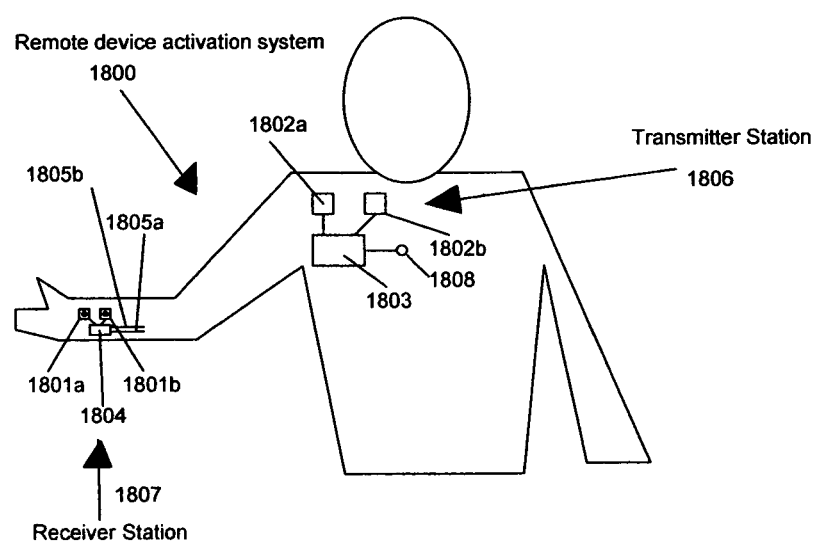
FIG. 18 is a schematic diagram for remotely activating devices according to an embodiment of the present invention.

FIG. 18 is a schematic diagram of a system 1800 that uses the present invention to activate a device using wireless signals. The system 1800 is described herein in a medical context. However, the system 1800 can have a wide range of applicability for activating devices remotely. For example, the system 1800 can be used with wireless devices placed in otherwise inaccessible locations to control their operation.

The system 1800 includes a receiver station 1807. The receiver station 1807 includes or is coupled to the wireless device to be activated. The receiver station includes a pair of electrodes 1805a and 1805b. The electrodes 1805a and 1805b are preferably a pair of neuroprosthetic electrodes, such as are used to restore motor control to paralyzed individuals. One end of each of the electrodes 1805a and 1805b is coupled to the body or medical device. The other end of each of the electrodes 1805a and 1805b is connected to the output of a receiver 1804 included in receiver station 1807.

The receiver station 1807 also includes receiver conductors 1801a and 1801b that are coupled to the receiver 1804. The receiver conductors 1801a and 1801b are preferably made of a biologically-compatible conductive material. Power for the receiver 1804 is preferably obtained from signals received by the receiver conductors 1801a and 1801b. Alternatively, power for the receiver 1804 is provided by an implanted battery pack or by inductive coupling. The needed materials and designs are known to those skilled in the art of implanted medical devices.

In operation, hardware or software logic within the receiver 1804 interprets commands initiated at a transmitter station 1806 to generate signals to the electrodes 1805a and 1805b of the proper format. The needed electrode signals and designs are known to those skilled in the art of neuroprosthetic control, see Kilgore, Kevin, et. al., "An Implanted Upper-Extremity Neuroprosthesis", Journal of Bone and Joint Surgery, Vol. 79-A, Nr. 4, April, 1997.

The system 1800 also includes a transmitter station 1806 that generates the required control signals to activate the wireless device. For medical device applications, the power lever of the transmitter 1803 is on the order of milliwatts. Further, in medical device application, the receiver conductors 1801a and 1801b have maximum dimensions of approximately 5 cm and the transmitter conductors 1802a and 1802b preferably will have dimensions of approximately 5 cm.

When used in medical device applications, the transmitter electronics 1803 and the transmitter conductors 1802a and 1802b are preferably mounted on the skin of the user. Alternatively, one or more of these components is embedded within the body. Input signals, for example, from a shoulder-motion sensor, see Kilgore, et. al., are interfaced to transmitter input connector 1808.

A single transmitter station 1806 using unique command codes or different frequencies to each receiver station 1807 can control multiple receiver stations 1807.

Those with ordinary skill in the art can use the present invention for other embodiments of medical device control, including, for example, as pacemakers, glucose and other blood sensors, and chemical release activators.

Figure 19:
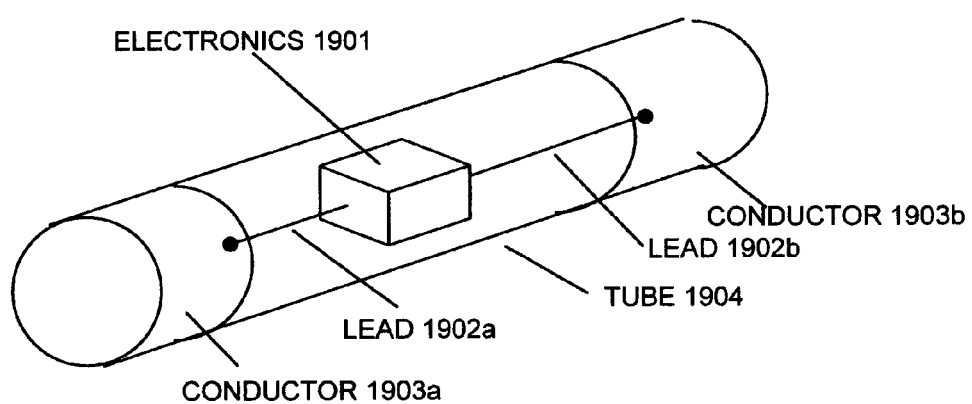
FIG. 19 is a schematic diagram of a conductor pair for use in an embodiment of the present invention.

FIG. 19 is a schematic diagram is another embodiment of the exemplary transmitting and receiving antennas that can be used in the present invention. An insulating tube 1904, such as PVC pipe provides structural support. Metal sheets 1903a and 1903b are wrapped around the tube, near its ends, to serve as conductors. The metal sheets 1903a and 1903b can be made of a material such as aluminum flashing. Insulated wires 1902a and 1902b running inside the tube connects the wiring to the conductors 1903a and 1903b, respectively. Electronics 1901 can either be included within the tube, or a transmission line can be run from the tube to external electronics. The electronics 1901 can be a receiver, transmitter, or transceiver.

Figure 20:
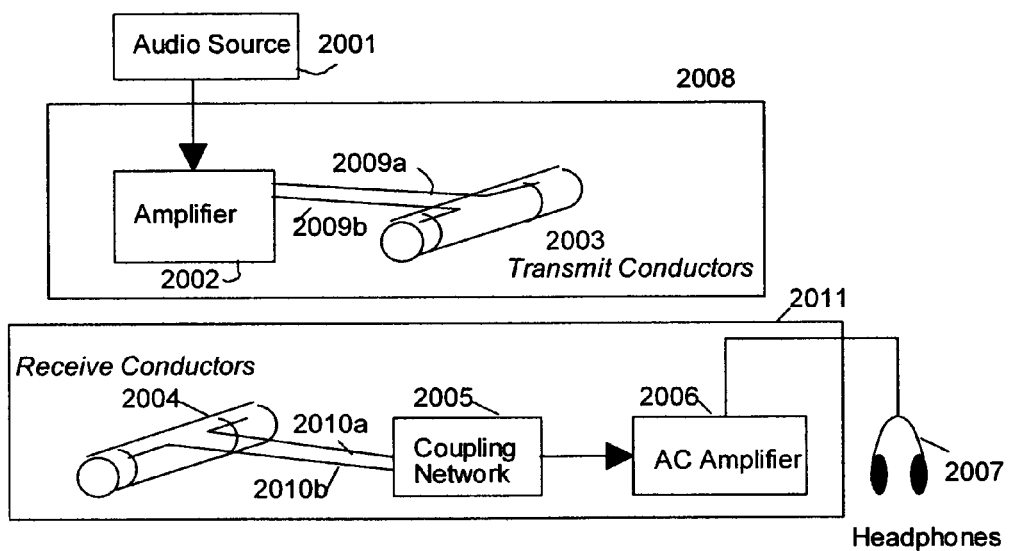
FIG. 20 is a schematic diagram of a system for transmitting signals using an electric field according to another embodiment of the present invention.

FIG. 20 is a schematic diagram of another embodiment of the present invention. An audio source 2001 generates an audio-frequency signal. The audio source 2001 can be any audio source. For example, the audio source 2001 can be an oscillator that generates a beacon. Alternatively, the audio source 2001 can be a microphone. The output of the audio source 2001 is sent to a transmitter 2008. The transmitter 2008 includes an amplifier 2002 and transmitter conductors 2003. The amplifier 2002 amplifies the output of the audio source 2001. The transmitter conductors 2003 are driven by the amplified audio signal through leads 2009a and 2009b. Where the audio source 2001 is an oscillator, for example, the transmitter conductors 2003 are driven at the frequency of the oscillator. A receiver 2011 receives the signal sent by the transmitter 2008. The receiver 2011 includes receiver conductors 2004. The receiver conductors 2004 receive the signal transmitted by the transmitter conductors 2003. The received signal travels through leads 2010a and 2010b and is coupled to an amplifier 2006 through a coupling network. The amplifier 2006 amplifies the received signal to directly drive headphones 2007 or a speaker so that the user can hear the information from the transmitter 2008. Coupling network 2005 can be a simple audio frequency transformer to match the impedance of the receiver conductors to the amplifier input, as can be done by one with ordinary skill in electronics design. In many locations, substantial 50 Hz or 60 Hz hum will be picked up by the conductors 2004, so that the coupling network 2005 preferably will reject those frequencies. Methods for rejecting the hum include, for example, high-pass or band pass filtering. Such methods are known to those with ordinary skill in analog electronics design. The coupling network 2005 and/or transmitter amplifier 2002 could be omitted to minimize complexity. However, the elimination of these elements can result in possible reduction in signal strength and range.

In another embodiment of the present invention, which focuses on the use of the system 1800 of FIG. 18 in a medical context, the human body is used as the imperfectly-conducting (partially-conducting) medium to form a wireless electrical stimulation system. In this embodiment of the present invention, wireless signals in a frequency spectrum that does not cause stimulation of muscle tissue are transmitted from one or more transmitter electrodes of the transmitter station 1806 and received at one or more receiver electrodes at a small receiver station or at each of a plurality of small receiver stations 1807. The one or more receiver electrodes are fully embedded in the body, partially embedded in the body, in contact with the skin of the body, or otherwise coupled directly to the body. The receiver station(s) 1807 use the energy of the transmitted signal and/or the commands encoded by the signal to cause electrical stimulation of the body, for purposes such as neuroprosthetics, cardiac pacemakers, etc. In this discussion, the term "electrode" will be used interchangeably with the term "conductor", because the term electrode is more commonly used in the medical field than the term conductor.

A key point in the success of this embodiment of the present invention is that the transmitted signal must be at a significantly different frequency than the frequency at which electrical stimulation pulses are generated that stimulate muscle tissue. Safety studies have shown that as the frequency of an electrical signal increases, its ability to stimulate muscles in the body decreases (see Reilly, J. P., "Electrical Stimulation and Electropathology." Cambridge University Press, 1992, pp. 126-128). Thus, if a sufficiently high transmission frequency is used, for example in the range of 10 kHz to 10 MHz, considerable electrical energy can be applied to the body without causing shocks or the stimulation of muscles. This embodiment of the present invention then converts this innocuous energy into one or more lower-frequency pulses at the desired location in the body to cause muscle tissue stimulation.

Figure 21:
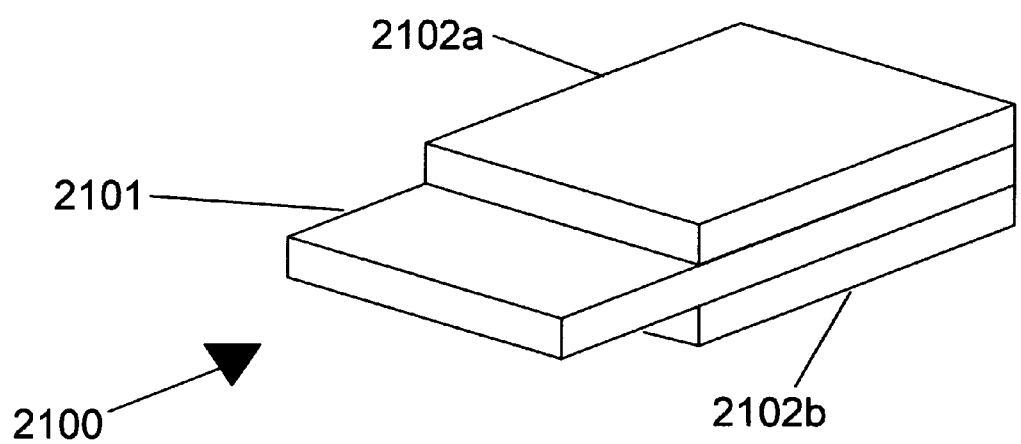
FIG. 21 is a drawing of a multi-purpose electrode that acts both as a small stimulation electrode and as a larger energy-receiving electrode.

In many cases, the shape of a typical stimulation electrode may be significantly different than the shape of an electrode designed for receiving electrical power and control. For example, stimulation electrodes (e.g. simulation electrodes 1805a and 1805b) often are a thin wire, whereas receiver electrodes (e.g. receiver electrodes 1801a and 1801b) may be of a much larger surface area. FIG. 21 is a drawing of a multi-purpose electrode 2100 that functions both as a small stimulation electrode and as a larger energy-receiving electrode. As described earlier, the frequency of operation of the electrical energy received by electrode 2100 is preferably in the range of tens of kHz to tens of MHz. At these frequencies, insulators 2102a and 2102b show only small impedance, so that the effective surface area of electrode conductor 2101 at the transmission frequency is approximately its entire surface area of the electrode conductor. However, stimulation pulses preferably have much lower frequency content, for example, a one millisecond pulse. At the lower frequencies of the stimulation, the insulators 2102a and 2102b show high impedance and, at the stimulation frequencies, the effective surface area of the electrode conductor 2101 is approximately the surface area of the uninsulated portion of the electrode conductor 2101. Thus, multi-purpose electrodes 2100 can be used as the one or more energy receiving electrodes (e.g. receiver electrodes 1801a and 1801b) and the one or more stimulation electrodes (e.g. simulation electrodes 1805a and 1805b) in the muscle tissue stimulation system of the present invention rather than using electrodes having different electrode structures for these applications. In addition, where desirable (e.g. for purposes of miniaturization), a single multi-purpose electrode 2100 can be used in the muscle tissue stimulation system of the present invention to function as both an energy-receiving electrode and a simulation electrode thereby replacing, with a single electrode, the two separate, different structured, electrodes normally used to perform these functions. In some applications, if the surface area constraints do not apply, a multi-purpose electrode without the insulators 2102a and 2102b may be appropriate.

In addition, the use of insulators 2102a and 2102b, preferably covering the entire electrodes 2101, could be used in a system even if the electrodes 2100 are not used as stimulation electrodes, because it may be advantageous to not have conductors in direct contact with the body, for example, to avoid undesirable chemical reactions.

The miniaturization technique shown in FIG. 15 is very applicable to this body stimulation system. The energy-receiving electrode or electrodes, the stimulation electrode or electrodes, or both can be combined with the electronics package to reduce overall package size, for example, using the electrode sharing technique shown in FIG. 22.

Where more than one receiver electrode is used at the receiver station or each of the receiver stations 1807, the amount of electrical energy available to the receiver station 1807 is a function of the strength of the electric field that the energy-receiver electrodes 1801a and 1801b are in, or equivalently, a function of the difference in electric potential between the electrode positions. This is particularly important for the case of a completely embedded receiver, because, unlike larger electronics attached to the surface of the body, such as entertainment or computing devices, which simply could use the body as a conductor, there is no reference potential within the body, and the differences in electrical potential within the body must be used. Therefore, strategic placement of receiver electrodes, to maximize the potential, will enable stronger stimulation signals to be generated. This will be referred to as a high-potential location. In general, a high-potential location exists wherever the geometry of the body or the non-uniformity of conductivity of the tissues, organs, or vessels in that area are such that the electrical potential between two or more points in that area is relatively large. Examples of high-potential locations include 1) placement of energy-receiving electrodes on opposite sides of a low-conductivity part of the body, such as on either side of a joint, 2) placement of the energy-receiving electrodes in points of differing conductivity, such as one in muscle, and one in fat and 3) placement of energy-receiving electrodes in an orientation at which greatest potential is available for that location in the body, 4) placement of one energy-receiving electrode near an extremity or near the surface of the body and the other energy-receiving electrode closer to the interior of the body, or other configurations of greater than average potential that will be apparent to those of skill in the art, and 5) use of a transmit frequency high enough to cause wavelength-related variations of voltage and current along paths in the body, and placement of electrodes at corresponding points of differing voltage. With such techniques, the energy available may be substantially greater than the average amount of energy, for the same inter-electrode spacing.

Figure 22:
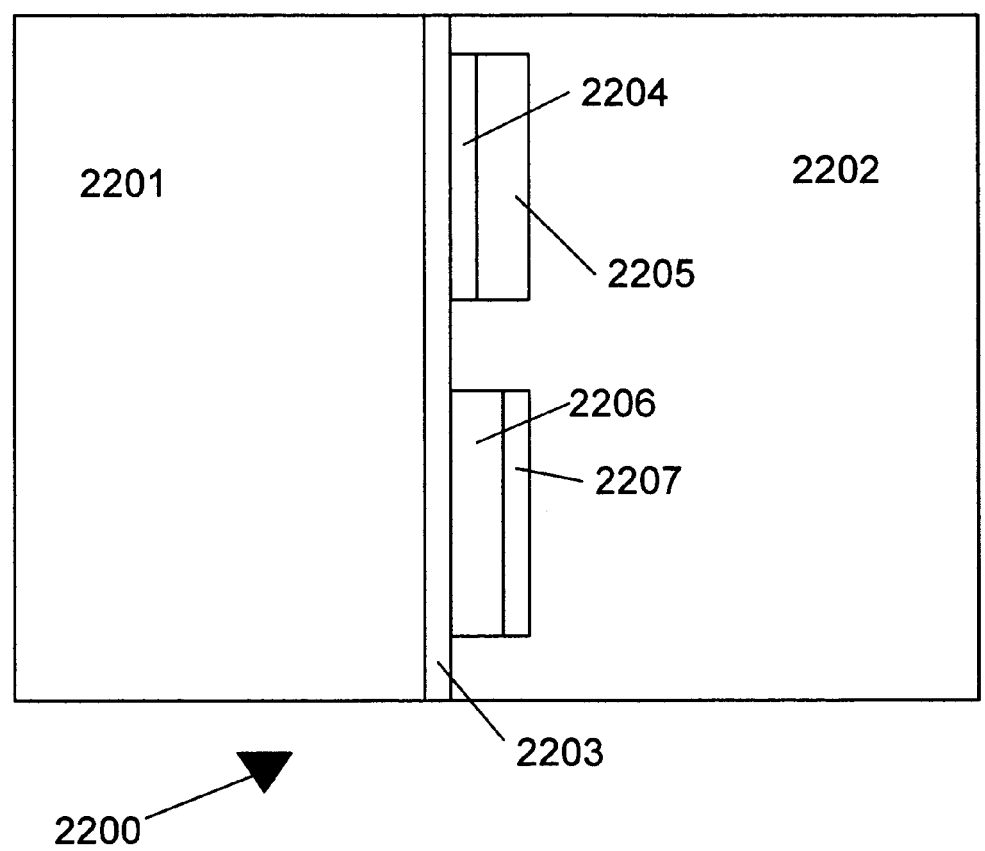
FIG. 22 is a drawing of a high-potential location in the body, showing a configuration of electrodes for that location.

In some situations, there may be nearby regions of the body having different potentials. For example, there may be a low-conductivity barrier between two areas that are at different potentials. The receiver electrodes may not need to physically be located within the two areas to take advantage of the high-potential properties. FIG. 22 is a diagram showing a high-potential configuration 2200. Areas 2201 and 2202 are at different potentials, and are separated by a boundary 2203, for example, a membrane in the body. Receiver electrodes 2204 and 2207 are connected to a receiver as described previously. An insulating layer 2205 on electrode 2204 provides isolation between the electrode 2204 and the area 2202. Thus, there is relatively greater capacitive coupling of electrode 2204 and area 2201. Similarly, an insulating layer 2206 on electrode 2207 provides additional isolation between the electrode 2207 and the area 2201, so there is relatively greater coupling of electrode 2207 and area 2202. Thinner insulating layers could also be added to electrodes 2204 and 2207 without substantially affecting the performance of high-potential configuration 2200.

A counterpoise, similar to counterpoise 1002 in FIG. 10, could also be used in a body stimulation system. For such an application, a conductor, preferably insulated, would be used similarly as described above. Additionally, the counterpoise could also be shared as a common ground to counterbalance a stimulation electrode, or could be shared between multiple receivers.

It may be desirable to have the voltage of the stimulation pulses at the stimulation electrode (an electrode such as the conductor of FIG. 10) or the stimulation electrodes (e.g. stimulation electrodes 1805a and 1805b) higher than the received voltage at energy receiving electrode or electrodes (e.g. receiver electrodes 1801a and 1801b). To achieve this increase in voltage, various impedance-increasing techniques may be used, as shown as impedance matching network 802 in FIG. 8. For the case of the embedded stimulation device, a transformer can be connected to the energy-receiving electrode(s) to step up the voltage. A preferable, and potentially smaller solution is an impedance-matching network using inductors and capacitors, such as the well-known pi network.

Further increases in voltage can be achieved in converting the alternating-current signal received by receiving electrode or electrodes (e.g. receiver electrodes 1801a and 1801b) into a DC or pulse form. For example, the well-known voltage doubler, voltage tripler, etc., made from diodes and resistors, can be placed either at the energy receiving electrode(s) (e.g. receiver electrodes 1801a and 1801b), or after another type of the impedance-increasing circuits described above. Another approach is to use higher voltage pulses of shorter duration at the transmitter. The average power flowing into the body would remain the same, but higher instantaneous voltages would be reaching the receivers.

It will be apparent to those of skill in the art that these impedance-changing circuits will also be applicable to many types of receiving systems and the techniques for using them will be apparent to those of skill in the art.

Figure 23:
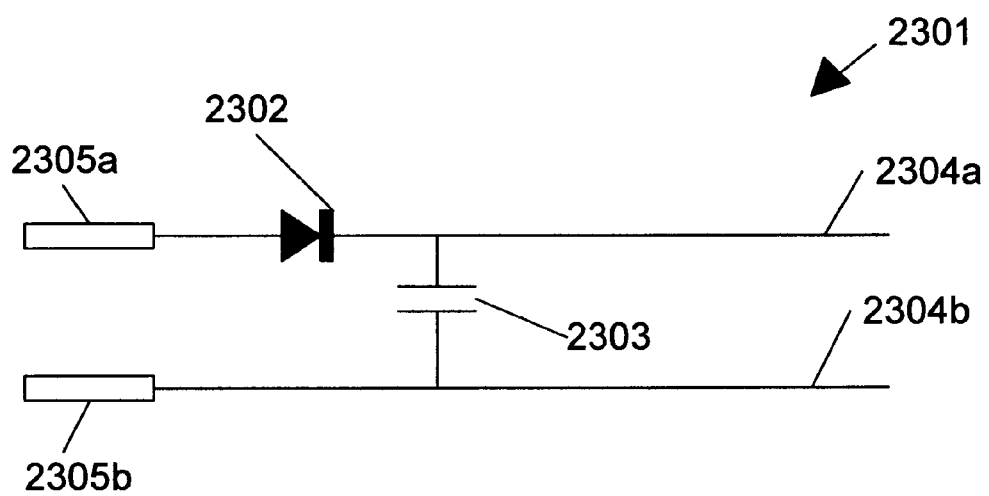
FIG. 23 is a schematic diagram of an envelope detector electronics module.

There are many possible configurations of the receiver 1804 to provide stimulation pulses. FIG. 23 is a schematic diagram of envelope detector electronics 2301 that can be used as a configuration of the receiver 1804. The transmitted signal, for example, from the transmitter station 1806 is amplitude modulated to have the desired stimulation pulse shape. The receiver electrodes 2305a and 2305b (which in this configuration correspond to receiver electrodes 1801a and 1801b) present the received signal to diode 2302 and capacitor 2303, which create a time-varying signal that follows the amplitude of the signal on the receiver electrodes 2305a and 2305b. The pulse at output leads 2304a and 2304b can then be applied to stimulation electrodes, for example a stimulation electrode such as that of FIG. 10 or the stimulation electrodes 1805a and 1805b of FIG. 18. Other implementations of envelope detectors will be apparent to those of skill in the art.

In some medical applications, it is desirable to have the smallest possible receiver station and as few electrodes as feasible. In this case, the energy receiving electrodes 1801a and 1801b and the stimulation electrodes 1805a and 1805b of FIG. 18 can preferably be the same electrodes. For example, multi-purpose electrode 2100 could be used in this configuration.

Figure 24:
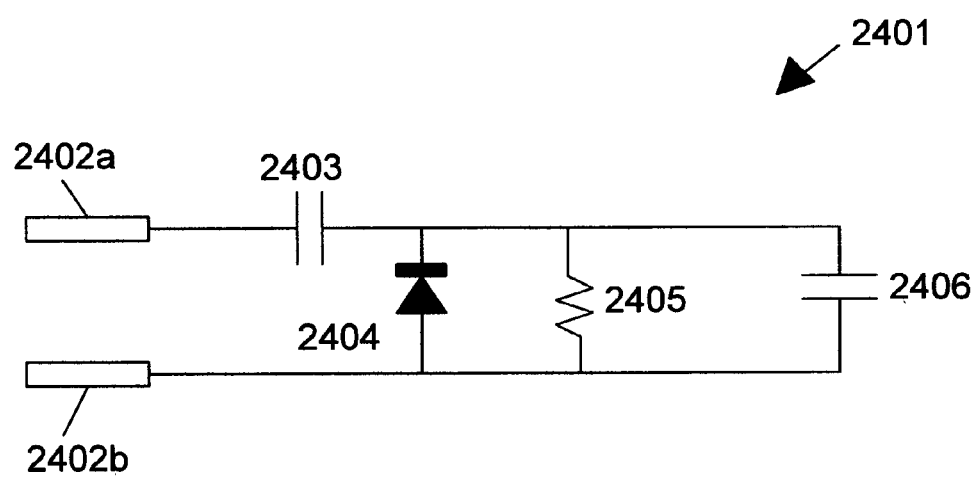
FIG. 24 is a schematic diagram of an electrical stimulation system that has only two electrodes.

FIG. 24 is a schematic diagram of a two-electrode receiver station 2401, which can be substituted in the receiver station 1807 for the receiver 1804 and the energy receiver electrodes 1801a and 1801b and its stimulation electrodes 1805a and 1805b. The received signal is a voltage across receiver electrodes 2402a and 2402b. Input capacitor 2403 forms a high-pass filter with resistor 2405. Diode 2404 rectifies this high-frequency signal and causes a pulse signal to be created across storage capacitor 2406. This circuit acts similarly to the envelope detector circuit shown in FIG. 23, and the pulse signal to be presented across electrodes 2402a and 2402b. Input capacitor 2403 also assures that the pulse signal across electrodes 2402a and 2402b is charge balanced, in other words, has no net DC effect. Using this type of technique, other circuits that create a pulse signal across their input electrodes will be apparent to those of skill in the art.

Figure 25:
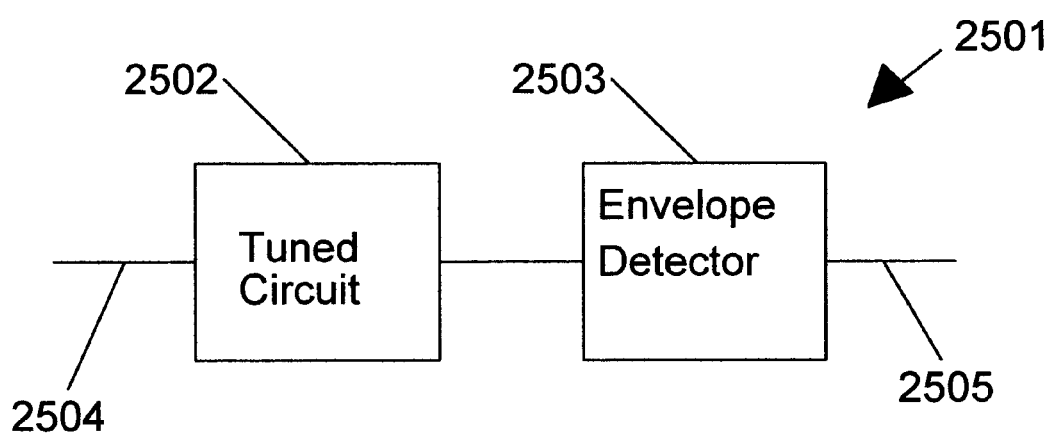
FIG. 25 is a schematic diagram of receiver electronics for an application where a frequency-modulated transmission is used.

FIG. 25 shows an alternate embodiment 2501 of the receiver 1804 of the receiver station 1807 for a case where a frequency-modulated (FM) transmission is used. In FM electronics the receiver 2501 of the receiver station 1807 has a tuned circuit 2502 placed ahead of an envelope detector 2503. This may be a simple parallel LC tuned circuit, or preferably a pi network that also is used for impedance step-up. The frequency of the transmitted signal from the transmitter station 1806 is modulated such that the peak of the pulse at the output of envelope detector 2503 occurs when the modulation frequency is at the center frequency of the tuned circuit 2502. The signal from receiver electrode or electrodes 1801a and 1801b is presented at input 2504, and the pulse output from envelope detector 2503 is output at output 2505 to the stimulation electrode or electrodes 1805a and 1805b. The implementation of this FM technique will be apparent to those of ordinary skill in the art.

In some stimulation applications, it may be desirable to provide a stimulation pulse with energy greater than what is instantaneously available from the receiver electrode or electrodes 1801a and 1801b. Because stimulation pulses are typically of a short duration, this can be achieved by storing energy within the receiver station 1807 in a capacitor or rechargeable battery, then releasing stimulation pulses when the needed energy has been accumulated.

Figure 26:
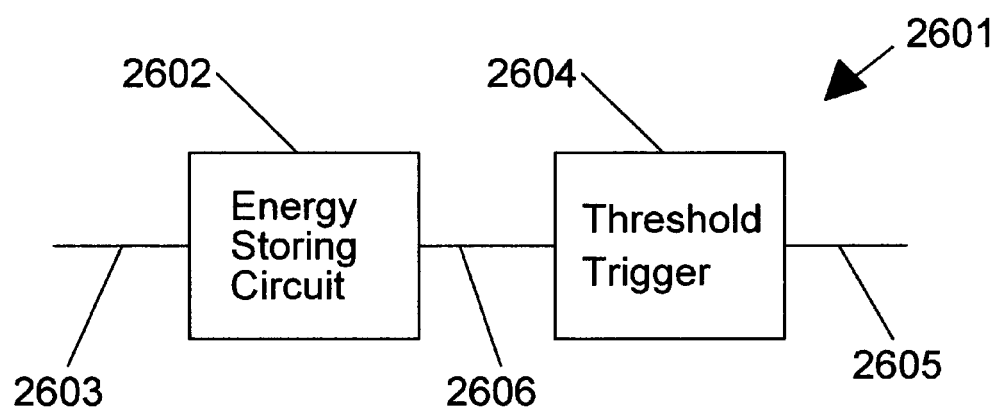
FIG. 26 is a schematic diagram of a pulse-generating electronics module.

FIG. 26 is a schematic diagram of pulse-generating electronics 2601 that can be used in the receiver station 1807. An energy storage circuit 2602 rectifies the incoming signal 2503 from the receiver electrode or electrodes 1801a and 1801b and stores it for later use. For example, the energy storage circuit 2602 could be a simple series diode and parallel capacitor. Threshold trigger 2604 is a circuit, for example, the well-known Schmitt trigger, which allows the input signal to flow to output 2605 and through the output 2605 to the stimulation electrode or electrodes 1805a and 1805b when the stored voltage 2606 exceeds a threshold, for example, 2 volts, and continue to flow until it reaches a lower voltage, for example, 0.2 volts. The construction of the energy storing circuit 2602 and the threshold detector 2604 will be apparent to those of ordinary skill in the art.

Figure 27:
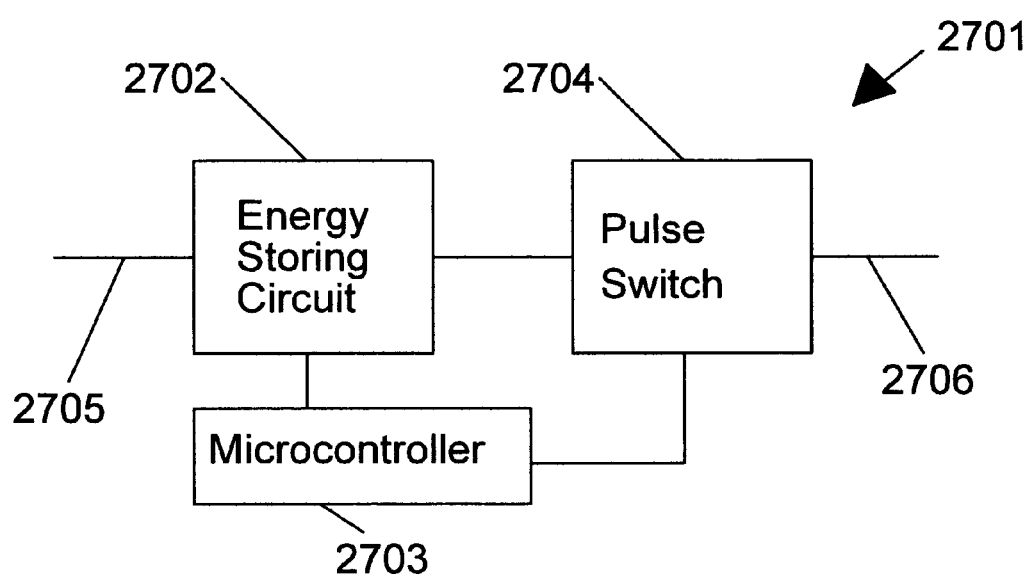
FIG. 27 is a schematic diagram of a microcontroller-based pulse-generating electronics module.

FIG. 27 is a schematic diagram of a microcontroller-based pulse-generating electronics 2701 that can be used in the receiver station 1807. Energy storing circuit 2702 accumulates electrical energy from input 2705 from the receiver electrode or electrodes 1801a and 1801b as described previously. A small amount of the stored energy is used to power a microcontroller 2703. The microcontroller 2703 monitors the amount of voltage in the energy-storing circuit 2702 and switches on Pulse Switch 2704 for a predetermined amount of time, for example, 1 millisecond, and the energy stored by the energy storing circuit 2702 is output to the output 2706 and the stimulation electrode or electrodes 1805a and 1805b. With a microcontroller, more sophisticated control and communication can also be achieved. For example, a demodulation circuit similar to the circuit in FIG. 25 can be used to demodulate commands and other communication, if the signal transmitted by the transmitting station 1806 is modulated by AM or FM. With such a communication link in place, for example, each receiving station 1807 may have a unique identifier, such that coordination among several receiving stations can be accomplished.

Due to the high frequency of the transmitted energy signal in the present invention, there is considerable flexibility in introducing the electrical energy to the body of the user. For example, there need not be a direct physical connection between the conductive material of transmitter electrode or electrodes 1802a and 1802b and the body of the user. Instead, a thin insulating layer, such as fabric, can be used between a flexible conductor and the skin. The capacitive coupling between the skin and the conductor will provide very little impedance to signal transmission at high frequencies, for example, at 1 MHz and above.

To create a transmitter monopole, as in the case of FIG. 10, the counterpoise could be the circuit ground of the transmitter electronics, or perhaps another conductor or a wire in the user's clothes.

Another use of an external-to-the-body transmitter is a transmitter dipole, in which two such transmitter electrodes are used. For high signal strength at a particular point in the body, the two dipole electrodes may be located on either side of the body, for example, one on the arm and one on an ankle, to activate receiving stations in the midsection of the body.

The transmitter station 1806 in FIG. 18 can be implemented in a variety of ways. For a life-support type application, for example a cardiac pacemaker, the transmitter station 1806 is preferably embedded within the body, so that it cannot be accidentally decoupled from the body. In this case, it is preferable for the transmitter electrodes 1802*a* and 1802*b* to be arranged to approximate a monopolar arrangement. This can be accomplished by mounting one electrode, for example transmitter electrode 1802*a*, relatively near the receiver station 1807, and the other electrode, for example transmitter electrode 1802*b*, more distant from the receiver station 1807. Alternately, if there are relatively few receiver stations 1807 in the body, and they are located in a localized area of the body, the transmitter electrodes 1802*a* and 1802*b* can be mounted as a dipole, with the receiver stations 1807 located between them, to deliver a maximum amount of energy. Of course, more than two transmitter electrodes 1802*a* and 1802*b* can be used to customize the electrical field, as shown above in FIG. 11.

There are several techniques for coordination of multiple receiver stations 1807 within the body. If frequency-selective circuits are used, such as a tuned input circuit or a frequency-dependent impedance matching circuit, each receiving station can be tuned for a different frequency, so that only the desired receiver station will be energized when the transmitter 1803 of the transmitter station 1806 is transmitting on the respective frequency. Alternately, if a microcontroller or other digital control circuit is included in the receiver stations 1807, commands for a specific receiver station or specific receiver stations may be issued, such that a pulse will be generated only by the receiver station or receiver stations that receive the appropriate command.

The foregoing disclosure of the preferred embodiments of the present invention has been presented for purposes of illustration and description. It is not intended to be exhaustive or to limit the invention to the precise forms disclosed. Many variations and modifications of the embodiments described herein will be apparent to one of ordinary skill in the art in light of the above disclosure. The scope of the invention is to be defined only by the claims appended hereto, and by their equivalents.

Further, in describing representative embodiments of the present invention, the specification may have presented the method and/or process of the present invention as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process of the present invention should not be limited to the performance of their steps in the order written, and one skilled in the art can readily appreciate that the sequences may be varied and still remain within the spirit and scope of the present invention.

What is claimed is:

1. A system for providing electrical stimulation to an imperfectly-conducting body comprising:
   a transmitter station, the transmitter station comprising:
      a transmitter electrode configured to be in direct contact with the imperfectly-conducting body, and
      a transmitter, coupled to the transmitter electrode and configured to produce a transmitter signal having a frequency spectrum that does not directly cause stimulation of muscle tissue within the imperfectly-conducting body and to cause a current to flow through the imperfectly-conducting body via the transmitter electrode, wherein the current generates an electric field in the imperfectly-conducting body, wherein the electric field transmits the transmitter signal within and through the imperfectly-conducting body without directly stimulating muscle tissue within the imperfectly-conducting body;
   a receiver station, the receiver station comprising:
      a receiver comprising a pulse generator configured to produce, in response to receipt of the transmitter signal through the imperfectly-conducting body from the transmitter, a muscle tissue stimulating waveform in a frequency spectrum that causes stimulation of muscle tissue within the imperfectly-conducting body and to cause electrical current corresponding to the muscle tissue stimulating waveform to flow from the pulse generator to a stimulation electrode,
      a receiver electrode coupled to the receiver and configured to couple the receiver to the transmitter, the receiver electrode responsive to the electric field in the imperfectly-conducting body, and
      a stimulation electrode, coupled to the pulse generator and configured to deliver the electric current corresponding to the muscle tissue stimulating waveform to the imperfectly-conducting body;
      wherein the receiver electrode has less impedance for electrical conduction to the imperfectly-conducting body at the frequency of the transmitter signal than the stimulation electrode has at the frequency of the stimulation waveform, and wherein the receiver electrode presents a different and greater effective surface area for electrical conduction for the transmitter signal than the stimulation electrode presents for the stimulation waveform.

2. The system for providing electrical stimulation to an imperfectly-conducting body according to claim 1,
   wherein the transmitter electrode comprises two transmitter electrodes,
   wherein the receiver electrode comprises two receiver electrodes, and
   wherein the stimulation electrode comprises two stimulation electrodes.

3. The system for providing electrical stimulation to an imperfectly-conducting body according to claim 1, wherein the receiver electrode and the stimulation electrode each comprise a multi-purpose electrode that is at least partially covered by a protective insulating layer, wherein the insulating layer has less impedance at the frequency of the transmitter signal than at the frequency of the stimulation waveform, whereby the multi-purpose electrode presents a different and greater effective surface area for the transmitter signal than for the stimulation waveform.

4. The system for providing electrical stimulation to an imperfectly-conducting body according to claim 1, wherein the receiver electrode and the stimulation electrode each comprise a multi-purpose electrode, the multi-purpose electrode further comprising an electrical conductor that is configured to couple the electric field in the imperfectly-conducting body to the receiver and to deliver the electric current corresponding to the muscle tissue stimulating waveform produced by the pulse generator.

5. The system for providing electrical stimulation to an imperfectly-conducting body according to claim 1, wherein the transmitter of the transmitter station is configured to be attached to and located outside the imperfectly-conducting body when the system is in use and the transmitter electrode is configured to be coupled to a skin of the imperfectly-conducting body when the system is in use whereby the transmitter of the transmitter station can be installed, removed, and serviced without surgical procedures.

6. The system for providing electrical stimulation to an imperfectly-conducting body according to claim 1, wherein the transmitter electrode of the transmitter station is configured to be located inside the imperfectly-conducting body when the system is in use whereby the transmitter electrode of the transmitter station will not suffer inadvertent disconnection from the imperfectly-conducting body.

7. The system for providing electrical stimulation to an imperfectly-conducting body according to claim 1, wherein the transmitter signal is an amplitude-modulated transmitter signal having a modulation envelope corresponding to the stimulation waveform, and
wherein the pulse generator of the receiver comprises an envelope detector whereby the stimulation waveform produced by the pulse generator is created from energy inputted to the envelope detector by the amplitude-modulated transmitter signal and the stimulation waveform produced by the pulse generator corresponds to the modulation envelope of the amplitude-modulated transmitter signal.

8. The system for providing electrical stimulation to an imperfectly-conducting body according to claim 1, wherein the transmitter signal is a variable frequency-modulated transmitter signal, and
wherein the pulse generator of the receiver produces a stimulation waveform that is a variable stimulation waveform that corresponds to the frequency modulation of the variable frequency-modulated transmitter signal.

9. The system for providing electrical stimulation to an imperfectly-conducting body according to claim 1, wherein the receiver further comprises an energy storage configured to store electrical energy received from the from the receiving electrode, wherein energy stored in the energy storage is used to provide the stimulation waveform generated by the pulse generator with more energy than is instantaneously available from the receiving electrode.

10. The system for providing electrical stimulation to an imperfectly-conducting body according to claim 1, wherein the transmitter signal has encoded digital information, and
wherein the pulse generator of the receiver comprises digital circuitry that decodes the digital information.

11. The system for providing electrical stimulation to an imperfectly-conducting body according to claim 1, wherein the receiver, the receiver electrode, and the stimulation electrode are housed within a single enclosure.

12. The system for providing electrical stimulation to an imperfectly-conducting body according to claim 1, wherein the receiver electrode comprises two receiver electrodes configured to be situated within a high-potential location of the imperfectly-conducting body to increase the electric field at the two receiver electrodes.

13. A method for providing electrical stimulation to an imperfectly-conducting body comprising:
producing a transmitter signal with a transmitter, the transmitter signal having a frequency spectrum that does not directly cause stimulation of muscle tissue within the imperfectly-conducting body;
coupling the transmitter signal to the imperfectly-conducting body, via a transmitter electrode in direct contact with the imperfectly-conducting body, to cause a current to flow directly into the imperfectly-conducting body thereby generating an electric field within the imperfectly conducting body, wherein the electric field transmits the transmitter signal through the imperfectly-conducting body without stimulating muscle tissues of the imperfectly-conducting body;
receiving the transmitter signal via a receiver electrode coupled to the imperfectly-conducting body and located within and responsive to the electric field so that current flows directly from the imperfectly-conducting body into the receiver electrode;
producing, by a pulse generator coupled to the receiver electrode and responsive to the transmitter signal, a muscle tissue stimulating waveform configured to stimulate muscle tissue within the imperfectly-conducting body; and
stimulating the muscle tissue within the imperfectly-conducting body with the muscle tissue stimulating waveform via a stimulation electrode coupled to the imperfectly-conducting body;
wherein the receiver electrode has less impedance for electrical conduction to the imperfectly-conducting body at the frequency of the transmitter signal than the stimulation electrode has at the frequency of the stimulation waveform, and wherein the receiver electrode presents a different and greater effective surface area for electrical conduction for the transmitter signal than the stimulation electrode presents for the stimulation waveform.

14. The method for providing electrical stimulation to an imperfectly-conducting body according to claim 13,
wherein the transmitter electrode comprises two transmitter electrodes,
wherein the receiver electrode comprises two receiver electrodes, and
wherein the stimulation electrode comprises two stimulation electrodes.

15. The method for providing electrical stimulation to an imperfectly-conducting body according to claim 14, wherein the receiver electrode comprises two receiver electrodes coupled to a location within a high-potential location of the imperfectly-conducting body to increase the electric field at the two receiver electrodes.

16. The method for providing electrical stimulation to an imperfectly-conducting body according to claim 13, wherein the receiver electrode and the stimulation electrode each comprise a multi-purpose electrode that is at least partially covered by a protective insulating layer, wherein the insulating layer has less impedance at the frequency of the transmitter signal than at the frequency of the stimulation waveform, whereby the multi-purpose electrode presents a different and greater effective surface area for the transmitter signal than for the stimulation waveform.

17. The method for providing electrical stimulation to an imperfectly-conducting body according to claim 13, wherein the receiver electrode and the stimulation electrode each comprise a multi-purpose electrode, the multi-purpose electrode further comprising an electrical conductor that is configured to couple the electric field in the imperfectly-conducting body to the receiver and to deliver the electric current corresponding to the muscle tissue stimulating waveform produced by the pulse generator.

18. The method for providing electrical stimulation to an imperfectly-conducting body according to claim 13, wherein the transmitter electrode is configured to be coupled to a skin of the imperfectly-conducting body whereby the transmitter can be installed, removed, and serviced without surgical procedures.

19. The method for providing electrical stimulation to an imperfectly-conducting body according to claim 13, wherein the transmitter electrode is configured to be coupled to a location inside the imperfectly-conducting body whereby the transmitter electrode will not suffer inadvertent disconnection from the imperfectly-conducting body.

20. The method for providing electrical stimulation to an imperfectly-conducting body according to claim 13, wherein the transmitter signal is an amplitude-modulated transmitter signal having a modulation envelope corresponding to a desired stimulation waveform, and wherein energy from the transmitter signal is converted to a desired stimulation waveform that corresponds to the modulation envelope of the amplitude-modulated transmitter signal to stimulate the muscle tissue of the imperfectly-conducting body via the stimulation electrode.

21. The method for providing electrical stimulation to an imperfectly-conducting body according to claim 13, wherein the transmitter signal is a variable frequency-modulated transmitter signal, and wherein the stimulation waveform is a variable stimulation waveform that corresponds to the frequency modulation of the variable frequency-modulated transmitter signal.

22. The method for providing electrical stimulation to an imperfectly-conducting body according to claim 13, further comprising storing energy from the receiving electrode to provide the stimulation waveform with more energy than is instantaneously available from the receiving electrode.

23. The method for providing electrical stimulation to an imperfectly-conducting body according to claim 13, wherein the transmitter signal comprises encoded digital information, and wherein the digital information is decoded to produce the muscle tissue stimulating waveform.

\* \* \* \* \*